United States Patent [19]

Paau et al.

[11] Patent Number: 5,061,490

[45] Date of Patent: Oct. 29, 1991

[54] BIOLOGICAL INOCULANT

[75] Inventors: Alan S. Paau; Dennis E. McCabe, both of Middleton; Steven G. Platt, Madison, all of Wis.

[73] Assignee: W. R. Grace & Co. - Conn., Columbia, Md.

[21] Appl. No.: 523,302

[22] Filed: May 5, 1990

Related U.S. Application Data

[63] Continuation of Ser. No. 79,538, Jul. 29, 1987, abandoned.

[51] Int. Cl.⁵ .................. A01N 63/00; C12N 1/12; C12N 1/00; C12R 1/07; A01C 1/06; C05F 11/08
[52] U.S. Cl. .................. 424/93; 435/252.1; 435/252.5; 435/835; 435/910; 47/57.6; 71/6
[58] Field of Search .............. 435/172.1, 172.3, 252.1, 435/252.5, 835, 910; 424/93; 47/57.6; 71/6

[56] References Cited

PUBLICATIONS

Smirnov et al. 1985. Biol. Abstr. 79(9): #80517.
Doudoroff et al. 1974, pp. 235–236 In: Bergey's manual of determinative bacteriology, 8th edition.
Buchanan et al., eds., Williams & Wilkins Co.: Baltimore.
Suslow et al. 1982, Phytopathology 72(2): 199–206.
Zahra et al. 1984 Zbl. Mikrobiol. 139(5): 349–357.
Raj et al. 1981. Soil Biol. Biochem. 13(2): 105–108.
Kwok et al. 1986. Phytopathology 76(10): 1123.
Debette et al., 1980. Biol. Abstr. 70(4): #26978.

Primary Examiner—Elizabeth C. Weimar
Assistant Examiner—David T. Fox
Attorney, Agent, or Firm—Quarles & Brady

[57] ABSTRACT

A biological inoculant is disclosed for facilitating and fostering the growth of edible corn plants. The inoculant includes biologically pure cultures of bacterial strains, including *Bacillus circulans*, a yet unidentified bacterial strain, and *Xanthomonas maltotphilia*.

7 Claims, No Drawings

BIOLOGICAL INOCULANT

This application is a continuation of application Ser. No. 07/079,538, filed Jul. 29, 1987, now abandoned.

FIELD OF THE INVENTION

The present invention relates to inoculants for improved cultivation and yield of corn in general, and specifically relates to particular bacterial strains which facilitate the germination and growth of edible corn plants.

BACKGROUND OF THE INVENTION

It has long been known in the art that certain biological, i.e. microbial, inoculants can be used with certain specific crops to facilitate the growth of crop plants or to assist the crops in resistance to particular pathogenic organisms. For example, it is quite common to inoculate soybean or other legumes at plantings with bacterial cultures of the genus Rhizobium, so that resulting Rhizobium cultures will nodulate within the roots of the soybean or other legume to form colonies which will fix nitrogen symbiotically for the plant as well as the bacteria.

It has also been proposed in the literature to co-cultivate microorganisms with other useful plants. For example, a method is described in U.S. Pat. No. 4,345,403 to Giovannetti to produce plants mycorrhized with symbiotic fungi. Such symbiotic co-cultivations are sometimes used to help the plant growth and alternatively sometimes used to produce fungi for consumption.

It is also known that soils in many areas suppress certain plant diseases. The disease suppression may be caused by bacteria in the genus Pseudomonas which colonize root surfaces, according to Schroth, Milton N. et al., "Disease-Suppressive Soil And Root-Colonizing Bacteria", *Science*, Volume 216, Jun. 25, 1982.

SUMMARY OF THE INVENTION

The present invention is directed to improving the growth of plants of edible corn, which includes the step of incorporating into the planting soil, into which the corn seeds are sown, a biologically effective culture of at least one biologically pure culture of bacteria selected from *Bacillus circulans*, a presently unidentified strain of bacteria and *Xanthomonas maltophilia* and mutant strains thereof. *Xanthomonas maltophilia* is also known as *Pseudomonas maltophilia* and these terms may be interchanged.

The present invention is also directed to corn seeds which can be coated with a coating including one or more of the above-mentioned bacterial strains to aid in the stand and yield from corn plants cultivated from those seeds.

It is an object of the present invention to provide an agent effective for the facilitation of germination and growth of edible corn plants.

It is another object of the present invention to provide a complete biological agent that will not only facilitate the growth of corn but will result in improved grain yields without additional synthetic chemical adjuvants.

Other objects, advantages, and features of the present invention will become apparent from the following specification when taken in conjunction with the accompanying claims.

DETAILED DESCRIPTION OF THE INVENTION

The present invention is directed to increasing corn grain yield by the use of a bacterial inoculant selected from one or more biologically pure bacterial strains selected from the group consisting of one strain *Bacillus circulans*, one strain of a presently unidentified strain of bacteria referred to here as BLA5A-4, and two strains *Xanthomonas maltophilia* and mixtures of these four strains.

The *Bacillus circulans* strain is characterized by the following description:

Morphological Characteristics:
The cells are gram negative motile rods $0.7 \times 3$-4 microns in size
Swollen sporangium contain oval to cylindrical spores centrally and sub-terminally located
Vegetative cells are seen singly with no chains observed
Cells have rounded and tapered ends
Staining is uniform
Culture grows poorly in nutrient broth or agar
Colonies are translucent, entire, smooth, glistening, almost flat
On Trypticase soil agar colonies appear mottled and irregular

| Physiology & Biochemistry: | | |
|---|---|---|
| Aerobic growth | + | |
| Anaerobic growth | + | |
| Anaerobic gas from $NO_3$ broth | − | |
| Growth at 30° C. | + | |
| Growth at 37° C. | + | |
| Growth at 45° C. | trace | |
| Growth at 0% NaCl | + | |
| Growth at 5% NaCl | − | |
| Growth at 7% NaCl | − | |
| Pigment | − | |
| Litmus milk | neutral reduced 7 days; acid reduced 14 days | |
| Growth at pH 6.0 | + | |
| Citrate | − | |
| Propionate | − | |
| Azide glucose | − | |
| Egg yolk reaction | − | |
| Starch hydrolysis | + | |
| Hippurate hydrolysis | − | |
| Gelatin hydrolysis | + | |
| Casein hydrolysis | − | |
| Tyrosine decomposition | − | |
| Catalase | + | |
| $KNO_3$—$KNO_2$ | + | |
| $KNO_3$ - gas | − | |
| Dihydroxyacetone | − | |
| Voges-Proskauer | − | |
| Methylene blue reduction | + | |
| Methylene blue reoxidation | + | |
| Carbohydrate Utilization: | acid | gas |
| arabinose | + | − |
| glucose | + | − |
| lactose | + | − |
| mannitol | + | − |
| sucrose | + | − |
| xylose | + | − |

The *Bacillus circulans* utilized in the present invention were isolated from the root of a soybean plant obtained from Louisiana. The spore position and general shape are not typical of most *Bacillus circulans* strains. Free spores are clearly oval, heavy walled on Tripticase soy agar and more cylindrical on nutrient agar. A further description of *Bacillus circulans* may be found in Gordon, R. et al, *The Genus Bacillus*, U.S. Dept. of Agriculture Handbook No. 427 (1973). To enable others to obtain a culture of this strain of *Bacillus circulans*, a sample of the *Bacillus circulans* bacteria has been deposited with the American Type Culture Collection (ATCC), accession number 53581, and with the Cetus Master Culture Collection (CMCC), accession number 2899.

All attempts at identifying the presently unidentified strain of bacteria designated BLA5A-4 on the basis of conventional biochemical and nutritional characteristics have proven unsatisfactory. The presently unidentified strain is characterized by the following description:

Morphological description

Gram-negative, non-motile coccobacillus with numerous inclusions

Cells can be found singly, in pairs and in twig-like chains of cells distorted by sudanophilic inclusions Growth is slow Colonies on nutrient agar are slightly rough and irregular in 96 hours On Stanier's Basal Medium with 0.5% yeast extract, colonies are smooth in 72 hours Pigments are not produced Biochemical characteristics:

Isolate is oxidase and catalase positive

Isolate does not grow on MacConkey's medium

Metabolism is respiratory but glucose is not oxidized in O-F medium

Simmons citrate and urease are positive

Gelatin, casein and starch hydrolysis are negative

Growth does not occur at 4°, 37° or 41° C.

Nitrate and nitrite are not reduced

Nutritional Characteristics:

Nutritional spectrum is extensive and versatile

Utilizes all carbohydrates and sugar derivatives tested

Utilizes alcohols, including methanol and polyalcohols

Utilizes dicarboxylic- and hydroxy- acids, but not fatty acids

Unable to grow autotrophically with hydrogen and $CO_2$ (tests were done at a $pO_2$ of 0.1 and 0.15)

General:

No identification with current strain data gave a taxonomic classification for this species. The strain utilizes as sole source of carbon a large number of carbohydrates and poly-alcohols. This versatility was not expressed in the O-F (Difco) tests, suggesting a sensitivity to the indicator, brom-thymol-blue. This trait has been found in *Pseudonomas pauciniobilis*, Flavobacterium species, and *Paraccoccus denitrificans*.

This strain resembles *P. denitrificans* in its morphology and ability to utilize methanol; however, it differs in that it does not denitrify or grow autotrophically.

The strain also has many features in common with the facultatively methylotrophic species in the genus Methylobacterium but its carbon utilization and lack of mobility and pigmentation differ from these species.

| Characterization Data: | | | |
|---|---|---|---|
| Gram positive | — | Tween 20 hydrolysis | w |
| Gram negative | + | Tween 80 hydrolysis | — |
| Gram variable | — | Indole | — |
| Motile at RT | — | Simmons citrate growth | + |
| 4° C. growth | — | Urease | + |
| 25° C. growth | + | Nitrate to nitrite | — |
| 30° C. growth | + | Nitrate reduction | — |
| 37° C. growth | — | Nitrite to nitrogen gas | — |
| 41° C. growth | — | Hydrogen sulfide (TSI) | — |
| Fluorescein | — | Lead acetate strip | + |
| Pyocyanine produced | — | Lysine decarboxylase | — |
| Diffusible orange | — | Arginine (Mollers) | — |
| Diffusible yellow | — | Ornithine decarboxylase | — |
| Diffusible purple | — | Phenylalanine deamination | — |
| Non-diffusible green | — | Lecithinase | — |
| Other non-diff. pigments | — | Phosphatase | w |
| Melanin pigment produced | — | Catalase | + |
| pH 6.0 growth | + | Oxidase | + |
| 3% NaCl growth | — | Gluconate oxidation | — |
| 6.5% NaCl growth | — | Growth on malonate as SCS | + |
| MacConkey agar growth | — | Tyrosine degradation | w |
| Skim milk agar growth | + | dl-hydroxybutyrate growth | + |
| Aesculin hydrolysis | w | PHB accumulation | + |
| Casein hydrolysis | — | Deoxyribonuclease | — |
| Starch hydrolysis | — | Growth on 0.05% cetrimide | — |
| Gelatinase | — | Growth on acetate as SCS | + |
| | | Testosterone deg. | — |

| Reactions in O-F Medium (Hugh & Leifson): | | | |
|---|---|---|---|
| Acid from L-arabinose | w | Acid from D-mannitol | w |
| Acid from cellobiose | w | Acid from Dmannose | k |
| Acid from ethanol | k | Acid from L-rhamnose | w |
| Acid from D-fructose | w | Acid from D-ribose | + |
| Acid from D-glucose AO2 | k | Acid from subrose | k |
| Acid from D-glucose AnO2 | — | Acid from trehalose | k |
| Alkaline pH in D-glucose | + | Acid from D-xylose | w |
| Acid from glycerol | k | | |
| Acid from i-inositol | w | Control | k |
| Acid from lactose | k | | |
| Acid from maltose | k | | |

+ = acid
w = weakly acid
k = alkaline
— = no change

| Sole Carbon Sources in Stanier's Mineral Base: | | | |
|---|---|---|---|
| L-arabinose | + | quinate | + |
| cellobiose | + | succinate | + |
| D-fructose | + | L-+-tartrate | — |
| D-glucose | + | valerate | — |
| lactose | + | B-alanine | + |
| maltose | + | D-A-alanine | + |
| D-mannitol | + | betaine | + |
| L-rhamnose | + | glycine | — |
| D-ribose | + | L-histidine | + |
| D-sorbitol | + | DL-norleucine | w |
| sucrose | + | L-proline | + |
| trehalose | + | D-tryptophan | w |
| D-xylose | + | L-valine | w |
| adonitol | + | DL-arginine | + |
| erythritol | + | benzylamine | — |
| glycerol | + | butylamine | — |
| ethanol | + | putrescine | + |
| geraniol | — | mesoconate | — |
| i-inositol | + | DL-glycerate | + |
| sebacic acid | — | L-tryptophan | w |
| acetamide | — | Hydrogen growth | — |
| adipate | — | Methanol 0.05% | + |
| benzoate | — | | |
| butyrate | — | ASM #784 | — |
| citraconate | — | | |
| D-gluconate | + | ASM #784 | — |
| M-hydroxybenzoate | — | Control | |
| 2-ketogluconate | + | | |
| DL-lactate | + | | |
| L-malate | + | | |
| pelargonate | — | | |
| propionate | — | | |

This strain was also isolated from the root of a soybean plant in Louisiana.

To enable others to obtain a culture of this presently unidentified strain of bacteria, a sample of the strain has been deposited with the ATCC, accession number 53578, and with the CMCC, accession number 2906.

Two other strains in the present invention have been identified as *Xanthomonas maltophilia*, also known as *Pseudomonas maltophilia*. The two isolates were found to be identical in all tests performed and were characterized by the following description:

Morphological Characteristics:

Non-spore forming Gram-negative rods actively motile with lophotrichous polar flagella On ATCC Medium No. 73, YGC medium, colonies are smooth, entire and yellow Fluorescein and pyocyanine are not produced, but melanin is produced Poly-B-hydroxy-butyrate does not accumulate Biochemical Properties:

Lysine decarboxylase, growth on MacConkey's agar and on Cetrinide is positive

Oxidase is negative

Hugh and Leifson's O-F glucose and maltose are positive, but D-mannitol is negative Tween 20, Tween 80, casein, aesculine, gelatin and deoxyribonucleic acid are hydrolyzed Nitrate is reduced to nitrite but denitrification does not take place Nutritional Properties:

Require methionine or cysteine as growth factors when grown in a mineral medium with various carbon sources Nutritionally very limited, utilizing only 16 of 54 carbon sources tested Like most Xanthomonads, the disaccharides cellobiose, lactose and maltose are utilized B-Hydroxybutyrate, polyalcohols and amines cannot be used Comparison of Isolates to Pseudomonas Cepacia and *Xanthomonas maltophilia*

| | P. cepacia | X. maltophilia | Isolates |
|---|---|---|---|
| Polar Lophotrichous | + | + | + |
| Yellow Colonies | + | + | + |
| Denitrification | − | − | − |
| Lysine Decarboxylase | + | + | + |
| O-F Glucose | + | + | + |
| O-F Maltose | + | + | + |
| Growth Factor Required: | | | |
| Methionine or Cystine | − | + | + |
| Oxidase Reaction | + | − | − |
| O-F Mannitol | + | − | − |
| PHB Accumulation | + | − | − |
| Nutritionally Limited | − | + | + |

Comparison of Characterization Data for *Xanthomonas maltophilia* ATCC 13637 (type strain) with Isolates

| | ATCC 13637 | Isolate 1 | Isolate 2 |
|---|---|---|---|
| Gram positive | − | − | − |
| Gram negative | + | + | + |
| Gram variable | − | − | − |
| Motile at RT | + | + | + |
| Flagella peritrichous | − | − | − |
| Flagella lophotrichous | + | + | + |
| Flagella monotrichous | − | − | − |
| Flagella lateral | − | − | − |
| 4° C. growth | − | − | − |
| 25° C. growth | − | − | − |
| 30° C. growth | + | + | + |
| 37° C. growth | + | + | + |
| 41° C. growth | − | − | − |
| Pigment diffusible | − | − | − |
| Pigment non-diffusible | + | + | + |
| Pigment color | Yellow | Yellow | Yellow |
| Pyocyanine produced | − | − | − |
| Fluorescein produced | − | − | − |
| Melanin pigment produced | − | + | + |
| pH 6.0 growth | + | + | + |
| 3% NaCl growth | + | + | + |
| 6.5% NaCl growth | − | − | − |
| MacConkey agar growth | + | + | + |
| Skim milk agar growth | + | + | + |
| Aesculin hydrolysis | + | + | + |
| Casein hydrolysis | + | + | + |
| Starch hydrolysis | − | − | − |
| Gelatinase | + | + | + |
| Tween 20 hydrolysis | + | + | + |
| Tween 80 hydrolysis | + | + | + |
| Indole | − | − | − |
| Simmons citrate growth | + | + | + |
| Urease | − | − | − |
| Nitrate to nitrite | + | + | + |
| Nitrite deduction | − | − | − |
| Nitrite to nitrogen gas | − | − | − |
| Hydrogen sulfide | − | − | − |
| Lysine decarboxylase | + | + | + |
| Argine (Mollers) | − | − | − |

Comparison of Characterization Data for *X. maltophilia* ATCC 13637 (type strain) with Isolates

| | ATCC 13637 | Isolate 1 | Isolate 2 |
|---|---|---|---|
| Ornithine decarboxylase | − | − | − |
| Phenylalanine deamination | − | + | + |
| Lecithinase | + | + | + |
| Phosphatase | + | + | + |
| Catalase | + | + | + |
| Oxidase | − | − | − |
| Gluconate oxidation | − | − | − |
| Growth on malonate as SCS | + | + | + |
| Tyrosine degradation | + | + | + |
| dl-hydroxybutyrate growth | − | − | − |
| PHB accumulation | − | − | − |
| Deoxyribonuclease | + | + | + |
| Growth on 0.05% cetrimide | − | + | + |
| Growth on acetate as SCS | + | + | + |
| Testosterone degradation | − | − | − |
| Acid from L-arabinose | − | − | − |
| Acid from cellobiose | w | + | + |
| Acid from ethanol | − | − | − |
| Acid from D-fructose | + | + | + |
| Acid from D-glucose AO2 | + | + | + |
| Acid from D-glucose AnO2 | − | − | − |
| Alkaline pH in D-glucose | − | − | − |
| Acid from glycerol | − | − | − |
| Acid from i-inositol | − | − | − |
| Acid from lactose | − | + | + |
| Acid from maltose | + | + | + |
| Acid from D-mannitol | − | − | − |
| Acid from D-mannose | + | − | + |
| Acid from L-rhamnose | − | − | − |
| Acid from D-ribose | − | w | w |
| Acid from sucrose | w | w | w |
| Acid from trehalose | w | w | w |
| Acid from D-xylose | − | − | − |

Comparision of Characterization Data for *X. malthophilia* ATCC 13637 (type strain) with Isolates 1 and 2

| Sole Carbon Sources: | | | |
|---|---|---|---|
| L-arabinose | − | − | − |
| Cellobiose | + | + | + |

| | ATCC 13637 | Isolate 1 | Isolate 2 |
|---|---|---|---|
| D-fructose | + | + | + |
| D-glucose | + | + | + |
| lactose | + | + | + |
| maltose | + | + | + |
| D-mannitol | − | − | − |
| L-rhamnose | − | − | − |
| D-ribose | − | − | − |
| D-sorbitol | − | − | − |
| sucrose | + | + | + |
| trehalose | − | + | + |
| D-xylose | − | − | − |
| adonitol | − | − | − |
| erythritol | − | − | − |
| glycerol | − | − | − |
| ethanol | − | − | − |
| geraniol | − | − | − |
| i-inositol | − | − | − |
| sebacic | − | − | − |
| acetamide | − | − | − |
| adipate | − | − | − |
| benzoate | − | − | − |
| butyrate | − | − | − |
| citraconate | − | − | − |
| D-gluconate | − | − | − |
| M-hydroxybenzoate | − | − | − |
| 2-ketogluconate | − | − | − |
| DL-lactate | + | + | + |
| L-malate | + | + | + |
| pelargonate | − | + | + |
| propionate | − | + | + |
| quinate | − | − | − |
| succinate | + | + | + |
| L-+-tartrate | − | − | − |
| valerate | − | + | + |

These two strains were also isolated from the root of a soybean plant in Louisiana.

To enable others to obtain a culture of the *Xanthomonas maltophilia* isolate 1 and *Xanthomonas maltophilia* isolate 2, samples have been deposited with the ATCC, accession numbers 53580 and 53579 respectively, and with the CMCC, accession numbers 2904 and 2905 respectively.

The bacterial inoculant, which can comprise any or all of the above-referenced bacterial strains, acts through an unknown mechanism to facilitate the germination and growth of plants of edible corn. While the mechanism by which this inoculant facilitates the germination and growth of corn plants is not very well understood, it is possible that the action involves an antagonistic action of the bacterial strains for other pathogens which may inhibit and/or retard the germination and growth of corn seedlings. It is also possible that the mechanism is a yet uncharacterized symbiotic relationship of some kind.

It is broadly intended within the scope of the present invention that the bacterial inoculant of the present invention be inoculated into the soil with corn seeds so that a bacterial culture will develop an intimate attachment to the root system of the corn plant as it grows. To facilitate this co-culturing, it is preferable that viable cells of the inoculant, preferably diluted with a suitable extender or carrier, either be applied to the seeds prior to planting or be introduced into the seed furrows at the time of planting the corn seeds. It is preferred that the bacterial strains be applied to the seeds, through the use of a suitable coating mechanism or binder of which there are several known to the art, prior to the seeds being sold in commerce for planting.

Alternatively, the bacterial strains, with or without a carrier, can be sold as a separate inoculant to be inserted directly into the furrows into which the corn is planted as the corn is planted. Whether the bacterial strains are coated actually on the corn seeds or are inserted into the furrows, the inoculant is preferably diluted with a suitable carrier or extender so as to make the bacterial strain easier to handle and to provide a sufficient quantity of material so as to be capable of easy human handling. Examples of suitable carriers include clay, vermiculite, perlite, charcoal, and water (aqueous solution).

The density of bacterial inoculation onto the seed or into the furrow should be sufficient to populate the sub-soil region adjacent to the roots of the corn plants. An effective amount of bacterial inoculant should be used. That amount is the amount sufficient to populate the root environment sufficiently to increase overall corn grain yield.

The practice of the present invention begins with the isolation of the bacterial strains suitable for use within this invention. The bacterial strains are isolated as intimate root-associates from a field crop analagous environment. The bacterial strains can be efficiently grown from a semi-solid support such as nutrient agar or in the liquid state such as nutrient broth (Difco). After a suitable bulk quantity of the appropriate desired strain has been cultured, the bacteria are harvested from the culture medium. The harvesting method selected depends upon the type of culture used. For instance, if a semi-solid support such as nutrient agar is used, the bacteria can be harvested by scraping the culture off the top of the agar. If a liquid culture is used, the bacteria can be separated from its culture medium by centrifugation.

Once the bacterial strains have been substantially separated from the culture medium, the bacteria are maintained at a temperature in the range of about 0° to 30° C. for a period in the range of about 0 to 96 hours under aseptic conditions. Preferably, the bacterial suspension is maintained at a temperature in the range of about 22° to 30° C., i.e., a normal room temperature, for a period of from about 3 to 25 hours under aseptic conditions, followed by further maintaining the bacterial suspension at a temperature in the range of about 0° to 15° C. for a period in the range of about 3 to 20 hours under aseptic conditions. The bacteria are maintained as concentrated liquid suspension during this step. At this stage, after the bulk of the liquid medium has been removed, the bacteria are no longer actively growing. The concentrated bacterial suspension should be a dense liquid appearing more like a viscous paste.

The concentrated bacterial suspension is then mixed with a porous, chemically inert granular carrier such that the weight ratio of concentrated bacterial suspension to dry carrier is in the range of about 0.5 to 1.5, preferably about 1.0.

Next, the bacteria-carrier mixture is slowly dried, preferably in air, at about room temperature, i.e., 22° to 30° C., for a period of about 2 to 10 days under asceptic conditions. The exact time period will, of course, vary depending upon the concentration of bacteria in the liquid culture. The drying should continue until the bacteria-carrier mixture appears totally dried. The remaining moisture content of the dried mixture should approximate the relative humidity of the environment.

The composition resulting after the completion of the drying includes dried, dormant yet viable bacteria together with a porous granular carrier. This granular product may or may not be reground to a more powdery form depending on the particular delivery strategy to be used.

The bacteria-carrier mixture can then be ground to a relatively fine powder for use in dusting or coating directly on the corn seeds with or without an adhesive or can be dusted on the field before or during planting. Alternatively, coarser granular bacteria-carrier mixture might not be ground, and then the dried granular can be easily and directly introduced into the furrows during planting to inoculate the seeds. Thus, the material produced from the drying of the bacteria-carrier mixture is readily adaptable to various delivery methods as may be desired for any given application.

A seed coating prepared by the present invention would include a mixture of the bacterial strain of the present invention together with a porous, chemically inert carrier, wherein the bacteria-carrier mixture has been air dried to a substantially moisture-free state. The weight ratio of concentrated bacteria culture to dry carrier is preferably in the range of about 0.5 to 1.5, more preferably about 1.0.

These bacterial strains may also be formulated for use as crop inoculants in other ways. The harvested bacteria may be mixed moist with fine peat, vermiculite, or perlite and used as a moist seed coating material. The bacteria could also be mixed with a granular carrier, such as granular peat, and supplied in a flowable form for introduction directly into the seed furrow or for mixing in the soil. The bacteria could also be simply diluted in water or other solution and sprayed into the seed furrow or the soil.

It has been discovered here that the co-cultivation of the bacterial strain of the present invention with corn plants results in significantly improved growth of corn plants. As will be appreciated by any person skilled in plant husbandry, the rate of growth or improvement in growth of any given crop is subject to many variables. It has been found here, however, that the co-cultivation of the bacterial strains of the present invention with edible corn plants is of significant advantage in at least some typical field conditions. It will be appreciated by one skilled in the art that a biological inoculant of the type described herein offers several significant potential advantages over the chemical inoculants or growth hormones or similar agents commonly used in agriculture today.

The following non-limitative examples are intended to illustrate the present invention.

EXAMPLE 1

The bacteria used in this example consisted of four strains described here, i.e., *Bacillus circulans*, a presently unidentified strain of bacteria BLA5A-4 and two isolates identified as *Xanthomonas maltophilia*, all of which were isolated from a field in Louisiana. In each of the eight tests comprising Example 1, the bacteria were cultured for 4 days on a nutrient. After culturing, the bacteria were harvested by scraping the culture from the agar of support. The first four tests were conducted under normal greenhouse conditions (N), i.e., temperatures of 20°-22° C. with supplemental light. The plants were watered periodically every 24 hours. Tests 5-8 were conducted under simulated drought conditions (D). These plants were watered once a week. The values of each test were obtained by comparing the average dry weight of 8 treated plants to the average dry weight of 16 untreated plants. The results illustrate that the bacterial inoculant can significantly increase the dry shoot weight of corn. The bacterial inoculant was applied as a liquid in seed furrows.

TABLE 1

| Changes In Dry Shoot Weight of Corn | | |
|---|---|---|
| Test | Condition | % Change |
| 1 | N[1],B[2] | 66 |
| 2 | N,B | 7 |
| 3 | N,B | 28 |
| 4 | N,K[3] | −4 |
| 5 | D[4],B | 46 |
| 6 | D,B | 7 |
| 7 | D,B | 3 |
| 8 | D,K | 1 |
| Ave. % Change | All Tests | 19.250[5] |
| Ave. % Change | Tests 1-4 | 24.250[6] |
| Ave. % Change | Tests 5-8 | 14.250[7] |

[1]N - Normal Greenhouse Conditions
[2]B - Bactavia Soil Type
[3]K - Kegonsa Soil Type
[4]D - Simulated Drought Conditions
[5]P = 0.033
[6]P = 0.107
[7]P = 0.137

EXAMPLE 2

Four field tests of corn were planted in which the plants were inoculated with strains of all four of the above-referenced bacteria dried in perlite and coated onto the corn seeds with polyvinylpyrrolidone 40,000. The control seeds were only coated with polyvinylpyrrolidone 40,000. After the normal growing season, the treated corn showed an average increase of 6.5 bushels per acres (B/A), amounting to an average 5.1% increase in yield. The results of the four field tests are listed in Table 2 below.

TABLE 2

| Yield Improvement of Corn | | | | |
|---|---|---|---|---|
| Test | Control Yield (B/A) | Treatment Yield (B/A) | B/A Yield Change | % Yield Change |
| 1 | 159.5 | 157.4 | −2.1 | −1.3 |
| 2 | 154.9 | 177.5 | 22.6 | 14.6 |
| 3 | 98.5 | 108.1 | 9.6 | 9.7 |
| 4 | 162.0 | 158.0 | −4.1 | −2.5 |
| Average | 143.7 | 150.2 | 6.5 | 5.1 |

EXAMPLE 3

Fourteen additional field tests were conducted in a manner similar to Example 2, with the exception that the bacterial strains dried in perlite were coated onto the seeds with a natural rubber cement (resin in hexane). The average increase of the treated fields as opposed to the control fields was 8.9 bushels per acre, which is a 7.0% average yield increase. The individual field tests and the results are listed below in Table 3.

TABLE 3

| Yield Improvement of Corn | | | | |
|---|---|---|---|---|
| Test | Control Yield (B/A) | Treatment Yield (B/A) | B/A Yield Change | % Yield Change |
| 1 | 109.2 | 121.1 | 12.0 | 11.0 |
| 2 | 104.3 | 120.2 | 15.9 | 15.2 |
| 3 | 144.8 | 148.3 | 3.5 | 2.4 |
| 4 | 137.3 | 144.3 | 7.0 | 5.1 |
| 5 | 173.4 | 160.6 | −12.8 | −7.4 |
| 6 | 187.7 | 195.3 | 7.5 | 4.0 |
| 7 | 165.0 | 175.1 | 10.1 | 6.1 |
| 8 | 113.2 | 132.3 | 19.2 | 17.0 |
| 9 | 160.8 | 159.6 | −1.2 | −0.8 |
| 10 | 97.2 | 113.1 | 16.0 | 16.4 |
| 11 | 155.1 | 164.8 | 9.7 | 6.3 |
| 12 | 177.3 | 198.5 | 21.2 | 12.0 |

TABLE 3-continued

| Test | Control Yield (B/A) | Treatment Yield (B/A) | B/A Yield Change | % Yield Change |
| --- | --- | --- | --- | --- |
| 13 | 158.9 | 166.6 | 7.7 | 4.9 |
| 14 | 156.6 | 165.8 | 9.2 | 5.9 |
| Average | 145.8 | 154.7 | 8.9 | 7.0 |

EXAMPLE 4

Fifteen additional field tests were conducted in a manner similar to Example 2, with the exception that the bacteria were not dried but were mixed with finely ground vermiculite with the bacterial density and proportions selected to give a final bacterial population of $10^8$ bacteria per gram of wet weight mixture. The moist inoculant was then coated onto seed with Pelgel (a trademark of and obtained from Nitragin Corporation) to adhere the mixture to the seed. The individual field tests are listed below in Table 4.

TABLE 4

| Test | Control Yield (B/A) | Treatment Yield (B/A) | B/A Yield Change | % Yield Change |
| --- | --- | --- | --- | --- |
| 1 | 156.6 | 153.5 | −3.1 | −2.0 |
| 2 | 144.8 | 139.4 | −5.4 | −3.7 |
| 3 | 155.1 | 170.3 | 15.2 | 9.8 |
| 4 | 177.3 | 194.7 | 17.4 | 9.8 |
| 5 | 202.2 | 218 | 15.8 | 7.8 |
| 6 | 97.2 | 101.6 | 4.4 | 4.5 |
| 7 | 187.8 | 188.7 | 0.9 | 0.5 |
| 8 | 160.8 | 159.2 | −1.6 | −1 |
| 9 | 158.9 | 169.4 | 10.5 | 6.6 |
| 10 | 173.4 | 155.5 | −17.9 | −10.3 |
| 11 | 137.3 | 142.4 | 5.1 | 3.7 |
| 12 | 113.2 | 124.2 | 11 | 9.7 |
| 13 | 165 | 169.3 | 4.3 | 2.6 |
| 14 | 104.3 | 117.8 | 13.5 | 12.9 |
| 15 | 109.2 | 122 | 12.8 | 11.7 |
| Average | 149.8 | 155.1 | 5.5 | 4.2 |

EXAMPLE 5

Nineteen additional field tests were conducted in a manner similar to Example 2, with the exception that the bacteria were diluted with water and sprayed into the seed furrow at the time of planting. The results of these field tests are listed in Table 5.

TABLE 5

| Test | Control Yield (B/A) | Treatment Yield (B/A) | B/A Yield Change | % Yield Change |
| --- | --- | --- | --- | --- |
| 1 | 124.1 | 142.1 | 18 | 14.5 |
| 2 | 173 | 176.7 | 3.7 | 2.1 |
| 3 | 141.6 | 146.1 | 4.5 | 3.1 |
| 4 | 117.6 | 128.9 | 11.3 | 9.6 |
| 5 | 155.1 | 153.2 | −1.9 | −1.3 |
| 6 | 191 | 192.2 | 1.2 | 0.6 |
| 7 | 110.2 | 109.8 | −0.5 | −0.4 |
| 8 | 177.4 | 184.5 | 7.2 | 4.0 |
| 9 | 109.3 | 109.3 | 0.0 | 0.0 |
| 10 | 192.7 | 204.5 | 11.8 | 6.1 |
| 11 | 149.8 | 150.1 | 0.3 | 0.2 |
| 12 | 129 | 131 | 2.0 | 1.5 |
| 13 | 137.2 | 137.1 | −0.1 | −0.1 |
| 14 | 123 | 127.9 | 4.8 | 3.9 |
| 15 | 103.3 | 106 | 2.7 | 2.6 |
| 16 | 137.7 | 139.3 | 1.6 | 1.2 |
| 17 | 147.9 | 153.4 | 5.5 | 3.7 |
| 18 | 132.1 | 128.5 | −3.6 | −2.7 |
| 19 | 140.7 | 150.2 | 9.5 | 6.8 |
| Average | 141.7 | 145.8 | 4.1 | 2.9 |

The four strains referred to here were all deposited with the American Type Culture Collection on Jan. 22, 1987, and are also deposited with the Cetus Master Culture Collection. They have been given accession numbers as follows:

| Strain | CMCC | ATCC |
| --- | --- | --- |
| B. circulans | 2899 | 53581 |
| BLA5A-4 | 2906 | 53578 |
| X. maltophilia (1) | 2904 | 53580 |
| X. maltophilia (2) | 2905 | 53579 |

The above deposits were made pursuant to a contract between the ATCC and Cetus Corporation, a partner in the assignee of the present invention. The contract with the ATCC provides for permanent availability of the progeny of these strains to the public on the issuance of the U.S. patent describing and identifying the deposit or the publication or laying open to the public of any U.S. or foreign patent application, whichever comes first, and for availability of the progeny of these strains to one determined by the U.S. Commissioner of Patents and Trademarks to be entitled thereto according to 35 USC §122 and the Commissioner's rules pursuant thereto (including 37 CFR §1.14 and 886 O.G. 638). The assignee of the present invention has agreed to that if the cultures of the strains on deposit should die or be lost or destroyed when cultivated under suitable conditions, they will be promptly replaced on notification with a viable culture of the same cell line.

It is to be understood that modifications and variations may be resorted to with respect to the present invention without departing from the spirit and scope of the invention as those skilled in the art will readily understand. Thus, the present invention should not be limited to the above-described specification, but should be interpreted in accordance with the following claims.

What is claimed is:

1. A biological inoculant for fostering the growth of corn consisting essentially of a culture of bacteria selected from the group consisting of biologically pure cultures of the following strains: a strain of unknown classification ATCC accession number 53578, *Xanthomonas maltophilia* ATCC accession number 53580, *Xanthomonas maltophilia* ATCC accession number 53579, and mutations thereof which retain the characteristic of enhancing the growth of corn.

2. The biological inoculant according to claim 1 wherein there is in addition a carrier selected from the group consisting of vermiculite, perlite and charcoal.

3. A method of improving the growth of plants of edible corn seeds comprising the step of introducing into the furrow into which the corn seeds are sown an effective amount of at least one biologically pure culture of bacterial strains selected from the group consisting of a strain of unknown classification ATCC accession number 53578, *Xanthomonas maltophilia* ATCC accession number 53580, *Xanthomonas maltophilia* ATCC accession number 53579, and mutations thereof which retain the characteristic of enhancing the growth of corn, and a carrier.

4. A biologically pure culture of the bacteria *Bacillus circulans* having all of the identifying characteristics of ATCC accession number 53581.

5. A biologically pure culture of a bacterial strain of unknown classification having all of the identifying characteristics of ATCC accession number 53578.

6. A biologically pure culture of the bacteria *Xanthomonas maltophilia* having all of the identifying characteristics of ATCC accession number 53580.

7. A biologically pure culture of the bacteria *Xanthomonas maltophilia* having all of the identifying characteristics of ATCC accession number 53579.

* * * * *